(12) United States Patent
Castiel et al.

(10) Patent No.: US 6,774,114 B2
(45) Date of Patent: Aug. 10, 2004

(54) TOPICAL APPLICATION OF IMMIXTURE OF ASCORBIC ACID + ASCORBIC ACID COMPOUNDS FOR AUGMENTING THE SYNTHESIS OF EPIDERMAL CERAMIDES

(75) Inventors: Isabelle Castiel, Jouy En Josas (FR); Corinne Ferraris, Paris (FR); Armelle Lavalle-Bouchard, Siene (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/425,608

(22) Filed: Apr. 30, 2003

(65) Prior Publication Data

US 2003/0190338 A1 Oct. 9, 2003

Related U.S. Application Data

(63) Continuation of application No. 09/828,881, filed on Apr. 10, 2001, now Pat. No. 6,596,695.

(30) Foreign Application Priority Data

Apr. 10, 2000 (FR) ............................................ 00/04575

(51) Int. Cl.$^7$ ........................ A01N 43/04; A01N 43/08; A61K 31/70; A61K 31/34
(52) U.S. Cl. ........................................ 514/27; 514/474
(58) Field of Search .................................. 514/27, 474

(56) References Cited

U.S. PATENT DOCUMENTS

| | | | |
|---|---|---|---|
| 4,780,549 A | 10/1988 | Terao et al. | |
| 5,084,563 A | 1/1992 | Sakai et al. | |
| 5,137,723 A | 8/1992 | Yamamoto et al. | |
| 5,432,161 A | 7/1995 | Sakai et al. | |
| 5,470,874 A | 11/1995 | Lerner | |
| 5,607,921 A | 3/1997 | Bernard et al. | |
| 5,801,192 A | 9/1998 | Dumas et al. | |
| 6,248,905 B1 | 6/2001 | Fujinami et al. | |

FOREIGN PATENT DOCUMENTS

| | | |
|---|---|---|
| EP | 0425066 | 5/1991 |
| EP | 0487404 | 5/1992 |
| JP | 44 000 220 | 1/1966 |
| JP | 46 024 699 | 7/1971 |
| JP | 61-263906 | * 11/1986 |
| JP | 05 059 075 | 3/1993 |
| JP | 09 110 628 | 4/1997 |

OTHER PUBLICATIONS

Patent Abstracts of Japan, JP 61 263906, abstract of JP 60105405, published Nov. 21, 1986.

Patent Abstracts of Japan, JP 08 333260, abstract of JP 07163046, published Dec. 17, 1996.

Patent Abstracts of Japan, JP 05 213736, abstract of JP 04057044, published Aug. 24, 1993.

Patent Abstracts of Japan, JP 07 252127, abstract of JP 06068204, published Oct 3, 1995.

Watanabe et al, "Stability of L–ascorbyl–2–O–α–glucoside and L–ascorbyl–2–phosphate Mg", *Chemical Abstracts*, vol. 125, No. 25, Dec. 16, 1996, published by the American Chemical Society, Columbus, Ohio.

Ponec et al, "The Formation of Competent Barrier Lipids in Reconstructed Human Epidermis Requires the Presence of Vitamin C", *The Journal for Investigative Dermatology, Inc.*, vol. 109, No. 3, pp. 348–355 (1997), published by Williams & Wilkins, Baltimore, Md.

* cited by examiner

Primary Examiner—Richard L. Raymond
Assistant Examiner—Zachary C. Tucker
(74) Attorney, Agent, or Firm—Burns, Doane, Swecker & Mathis, L.L.P.

(57) ABSTRACT

Synergistic immixtures of ascorbic acid with at least one monosaccharide ester of ascorbic acid and/or at least one metal salt of phosphorylated ascorbic acid more effectively increase the synthesis of epidermal ceramides in human skin, especially types IV to VII ceramides, as well as improve the barrier function, moisture content and/or suppleness/surface appearance of the skin and which otherwise combat/prevent intrinsic aging thereof and are useful for the treatment of dermatitis.

28 Claims, No Drawings

TOPICAL APPLICATION OF IMMIXTURE OF ASCORBIC ACID + ASCORBIC ACID COMPOUNDS FOR AUGMENTING THE SYNTHESIS OF EPIDERMAL CERAMIDES

CROSS-REFERENCE TO RELATED APPLICATION

This application is a continuation of U.S. application Ser. No. 09/828,881, filed Apr. 10, 2001, now U.S. Pat. No. 6,596,695 expressly incorporated by reference herein in its entirety and relied upon.

CROSS-REFERENCE TO PRIORITY APPLICATION

This application claims priority under 35 U.S.C. §119 of FR-00/04575, filed Apr. 10, 2000, hereby expressly incorporated by reference.

CROSS-REFERENCE TO COMPANION APPLICATION

Copending application Ser. No. 09/828,884, filed concurrently with parent application Ser. No. 09/828,881 on Apr. 10, 2001 and assigned to the assignee hereof.

BACKGROUND OF THE INVENTION

1. Technical Field of the Invention

The present invention relates to the administration, via topical application onto human skin, of immixture of ascorbic acid itself in combination with at least one monosaccharide ester of ascorbic acid and/or at least one metal salt of phosphorylated ascorbic acid, or compositions comprised thereof, for, inter alia, increasing the synthesis of epidermal ceramides.

2. Description of the Prior Art

Human skin consists of two strata or layers, namely, a deep layer, the dermis, and a superficial layer, the epidermis.

The dermis provides the epidermis with a solid support. It is also its feeder component. It consists principally of fibroblasts and an extracellular matrix which is itself principally composed of collagen, elastin and a substance deemed the "ground" substance, these components being synthesized by the fibroblasts. Leukocytes, mastocytes or tissue macrophages are also present therein. The dermis also contains blood vessels and nerve fibers.

The epidermis is exposed to the external environment. Its role entails protecting the body from dehydration and from external factors, whether they are chemical, mechanical, physical or infectious attacks/challenges.

Natural human epidermis is composed mainly of three types of cells which are the keratinocytes, which are highly predominant, the melanocytes and the Langerhans' cells. Each of these cell types contributes, through its specific functions, to the essential role played by the skin in the organism.

The cells constituting the epidermis are delimited by a lipid domain. During differentiation, phospholipids, one role of which is to form the fluid structure of the cell membranes of the living layers of the epidermis, are progressively replaced by a mixture which is predominantly composed of fatty acids, cholesterol and sphingolipids.

These lipids are organized into specific lamellar structures whose integrity depends not only on the quality of the fractions present, but also on their respective proportions. This lamellar structure of the lipids of the lipid domain of the epidermis is responsible for the fluidity and, therefore, suppleness of the skin.

Lipids are also responsible for the "barrier" properties of the epidermis, particularly the stratum corneum.

Epidermal lipids are synthesized principally in the living epidermis. They essentially consist of phospholipids, sphingolipids, cholesterol, free fatty acids, triglycerides, esters of cholesterol and alkanes.

The phospholipids are essential for the constitution of the cell membranes. They play an important role in the mediation of extracellular signals and the formation of free aliphatic chains utilized for the production of energy. They constitute a reservoir of free fatty acids which are necessary for the constitution of sphingolipids.

Sphingolipids (or ceramides) are essential for maintaining the multilamellar structure of the intercorneocyte lipids. They are also essential for water-related exchanges and the "barrier" function of the epidermis.

Cholesterol plays a crucial role in skin hydration and in the "barrier" function of the epidermis.

And free fatty acids play a major role in maintaining the lamellar structure of the lipids of the stratum corneum, and in the constitution of the cell membranes where they are responsible for membrane fluidity and also for physiological processes such as receptor function or enzyme activity.

The essential role played by skin lipids and the importance which their integrity constitutes, are thus manifest.

However, in certain situations, whether in the event of specific pathological conditions (atopic dermatitis), skin aging, actinic aging, dry skin or else a barrier function which is impaired through repeated physical or chemical attacks, the human epidermis exhibits modifications in its lipid synthesis mechanism(s) and/or composition.

To improve the lipid content of the epidermis and consequently to favorably contribute to the suppleness of the skin, two mechanisms of action may be considered. The first is the exogeneous supply of lipid compounds by the topical route. The second entails stimulating the synthesis of endogeneous lipids. It has thus been demonstrated that it was possible to improve the lipid profile of reconstructed epidermes by adding ascorbic acid (vitamin C) to the culture medium (*J. Invest. Dermatol.*, 109:348-355, 1997). However, because of its chemical structure (alpha-ketolactone), ascorbic acid is very sensitive to certain environmental parameters such as light, heat and aqueous media, in particular alkaline and/or aerobic media. Because of these problems of stability, it is necessary to use high concentrations of ascorbic acid in order to observe the effect, on the skin, of a composition comprised thereof.

SUMMARY OF THE INVENTION

It has now surprisingly and unexpectedly been determined that the combination or immixture of at least one particular derivative of ascorbic acid with ascorbic acid itself elicits a synergy of action on epidermal lipogenesis and more especially on the synthesis of epidermal ceramides. This synergy allows the use of a lesser amount of ascorbic acid in favor of derivatives thereof which are more stable and therefore easier to formulate into cosmetic or dermatological compositions.

Briefly, then, the present invention features augmenting epidermal lipogenesis (increasing the synthesis of epidermal ceramides) by topically applying onto the skin of an individual subject in need of such treatment, an effective amount of intimate admixture of ascorbic acid itself and at least one compound selected from a monosaccharide ester of ascorbic acid and a metal salt of phosphorylated ascorbic acid.

DETAILED DESCRIPTION OF BEST MODE AND SPECIFIC/PREFERRED EMBODIMENTS OF THE INVENTION

More particularly according to the present invention, exemplary monosaccharide esters of ascorbic acid include, in particular, the glycosylated, mannosylated, fructosylated, fucosylated, galactosylated, N-acetylglucosaminated and N-acetylmuramic derivatives of ascorbic acid and mixtures thereof, and more especially ascorbyl 2-glucoside or 2-O-α-D-glucopyranosyl of L-ascorbic acid, or, alternatively, 6-O-β-D-galactopyranosyl of L-ascorbic acid. The latter compounds as well as processes for the preparation thereof are, in particular, described in EP-A-0,487,404, EP-A-0,425,066 and JP-05,213,736.

In turn, the metal salt of phosphorylated ascorbic acid is advantageously selected from among the ascorbyl phosphates of an alkali metal, the ascorbyl phosphates of an alkaline earth metal and the ascorbyl phosphates of a transition metal. Magnesium ascorbyl phosphate is preferably employed.

In a preferred embodiment, the intimate admixture according to the invention comprises ascorbic acid and a monosaccharide ester of ascorbic acid and a metal salt of phosphorylated ascorbic acid.

The present invention thus also features a regime/regimen for augmenting/increasing the synthesis of epidermal ceramides, comprising topically applying effective amount of synergistic immixture of ascorbic acid/ascorbic acid derivative(s) onto the skin of an individual subject in need of such treatment.

By the expression "epidermal ceramides" according to the present invention are intended both types I to VII ceramides, in particular types IV to VII ceramides, and acylglucosylceramides.

This invention also features compositions comprising the above immixtures, formulated into a physiologically acceptable medium therefor (vehicle, diluent or carrier).

Taking account of the properties of the aforesaid combinations in lipogenesis, the compositions according to the invention are also useful for improving the barrier function of the skin. Such preparations may be for the treatment of certain pathological conditions involving disruption of the barrier function, such as atopic or seborrhoeic dermatitis. Same are also useful for cosmetic purposes, in particular for improving the suppleness of the skin and/or the surface appearance of the skin and/or for combating or preventing skin aging.

As improvement in the barrier function promotes better retention of water in the skin, the compositions according to the invention are useful as cosmetics for moisturizing the skin.

In all of the above applications, the compositions according to the invention preferably contain from 0.0001% to 15% by weight, and more preferably from 0.5% to 5% by weight of ascorbic acid relative to the total weight of the composition; from 0.001% to 10% by weight, and more preferably from 0.01% to 0.5% by weight of monosaccharide ester of ascorbic acid relative to the total weight of the composition; and from 0.001% to 10% by weight, more preferably from 0.01% to 0.5% by weight of metal salt of phosphorylated ascorbic acid relative to the total weight of the composition.

The compositions of the invention may be formulated into any of the galenic forms normally employed for topical application, in particular in the form of an aqueous, aqueous/alcoholic or oily solution, an oil-in-water or water-in-oil or multiple emulsion, an aqueous or oily gel, an anhydrous liquid, pasty or solid product, a dispersion of oil in an aqueous phase with the aid of spherules, it being possible for these spherules to be polymeric nanoparticles such as nanospheres and nanocapsules, or more preferably lipid vesicles of the ionic and/or nonionic type.

The subject compositions may be fluid to a greater or lesser degree and may have the appearance of a white or colored cream, an ointment, a milk, a lotion, a serum, a paste, or a mousse or foam. Same may optionally be applied onto the skin in the form of an aerosol. They may also be provided in the form of a solid, in particular in the form of lipstick when it is, for example, intended to treat chapped lips. They can also be used as care products for the face or the body and/or as makeup products for the skin.

In known fashion, the compositions of the invention may also contain the customary adjuvants and additives in the cosmetic field, such as hydrophilic or lipophilic gelling agents, hydrophilic or lipophilic bioaffecting active agents, preservatives, antioxidants, solvents, perfumes, fillers, UV-screening agents, pigments, odor absorbers and colorants. The amounts of these various adjuvants and additives are those conventionally used in the field considered, and range, for example, from 0.01% to 20% of the total weight of the composition. These additives and adjuvants, depending on their nature, may be introduced into the fatty phase, into the aqueous phase, into the lipid vesicles and/or into the nanoparticles. In any event, these additives and adjuvants, as well as their proportions, are selected such as not to impair the desired properties for the combination of active agents according to the invention.

When a composition of the invention is an emulsion, the proportion of the fatty phase may range from 5% to 80% by weight, and preferably from 5% to 50% by weight relative to the total weight of the composition. The oils, emulsifiers and coemulsifiers formulated into the emulsions are those conventionally employed in the field considered. The emulsifier and the coemulsifier are typically present in the subject compositions in a proportion ranging from 0.3% to 30% by weight, and preferably from 0.5% to 20% by weight relative to the total weight of the composition.

Exemplary oils according to the invention include the mineral oils (liquid paraffin), oils of plant origin (avocado oil, soyabean oil), oils of animal origin (lanolin), synthetic oils (perhydrosqualene), silicone oils (cyclomethicone) and fluorinated oils (perfluoropolyethers). Exemplary fatty substances include the fatty alcohols (cetyl alcohol), fatty acids, and waxes (carnauba wax, ozokerite).

Exemplary emulsifiers and coemulsifiers according to the invention include, for example, esters of a fatty acid and a polyethylene glycol such as PEG-20 stearate, and esters of a fatty acid and glycerin such as glyceryl stearate.

Exemplary hydrophilic gelling agents include, in particular, carboxyvinyl polymers (carbomer), acrylic copolymers such as acrylate/alkyl acrylate copolymers, polyacrylamides, polysaccharides, natural gums and clays, and exemplary lipophilic gelling agents include the modified clays such as bentones, metal salts of fatty acids, hydrophobic silica and polyethylenes.

And exemplary active agents include, in particular, keratolytic and/or desquamatory agents, depigmenting agents, UV-screening agents, anti-free radical agents and mixtures thereof. In the event of incompatibility, at least some of the active agents may be incorporated into spherules, in particular ionic or nonionic vesicles and/or nanoparticles (nanocapsules and/or nanospheres), such that the active agents which are mutually incompatible are isolated from each other in the composition.

In another embodiment of the invention, the aforesaid compositions are administered to improve the content of lipids and/or the barrier function of reconstructed epidermes. The conjoint addition of ascorbic acid and at least one of the derivatives thereof to culture media for reconstructed epidermes thus makes it possible to ensure these epidermes resemble more closely the structure of normal human skin and thereby to permit the in vitro tests (in particular the penetration studies) carried out on these epidermes more predictive of the phenomena which will be observed in vivo.

In this case, the compositions according to the invention preferably contain from 0.0000001% to 0.1% by weight, and more preferably from 0.0005% to 0.05% by weight of ascorbic acid relative to the total weight of the composition; from 0.0000001% to 0.01% by weight, and more preferably from 0.000005% to 0.005% by weight of monosaccharide ester of ascorbic acid relative to the total weight of the composition; and from 0.0000001% to 0.01% by weight, more preferably from 0.000005% to 0.005% by weight of metal salt of phosphorylated ascorbic acid relative to the total weight of the composition.

In order to further illustrate the present invention and the advantages thereof, the following specific examples are given, it being understood that same are intended only as illustrative and in nowise limitative.

EXAMPLE 1

Demonstration of the Synergy of Action of the Mixture of Vitamins C, CP and CG on the Synthesis of Epidermal Ceramides:

Ascorbic acid and derivatives thereof were tested on a skin equivalent marketed by EPISKIN (LYON, France), after culturing the latter for 7 days. The culture and test media were those included in the kit marketed by the supplier. Each compound was tested individually at 15 μg/ml and in combination with 5 μg/ml (as vitamin C equivalent), in the culture medium. The reconstructed epidermes were treated for 24 hours. The control consisted of an identical epidermis equivalent which was subjected to topical application of culture medium without the test compound.

The reconstructed epidermis was incubated overnight with $^{14}C$ acetate (2 μCi/ml) before topical application of vitamin C and derivatives thereof, to monitor the synthesis of the lipids.

At the end of the incubation period, the epidermis equivalent was detached from its collagenic support. The preparation of the lipids of the epidermis equivalent and their analysis by HPTLC or high-performance thin-layer chromatography, were carried out according to the technique and with the buffers described by M. Ponec (1991, *Adv. Lipid Res.*, 24:83–117).

At the end of the migration, densitometric analysis of the autoradiograph was carried out using a densitometer of the FUJI brand, model 1800.

Table 1 below reports the results obtained, for the three vitamin C derivatives tested, each at 15 μg/ml, as a percentage increase in ceramides relative to the untreated control.

TABLE 1

| Test Compound | % increase in ceramides in the epidermis equivalent |
|---|---|
| Vitamin C | 54% |
| Vitamin CP | 99% |
| Vitamin CG | 69% |

The (cumulative) theoretical value for the mixture of the three vitamin C compounds at 5 μg/ml was, therefore: (54+99+69)/3=74.

However, the real value obtained for the mixture of the three vitamin C compounds, tested at 5 μg/ml each, was 114.

This example therefore clearly demonstrates that after only 24 hours of treatment, the combination of the various types of vitamin C elicits a synergy of action on the synthesis of the epidermal ceramides.

EXAMPLE 2

Demonstration of the Synergy of Action of the Mixture of Vitamins C and CP on the Synthesis of Epidermal Ceramides:

The procedure described in Example 1 was repeated, except that the test was performed over 48 hours instead of 24 hours. In addition, only vitamin C and vitamin CP were tested, the mixture of the two being formulated using 7.5 μg/ml of each vitamin.

Table 2 below groups together the results obtained, for the two vitamin C compounds tested, each at 15 μg/ml as a percentage increase in the ceramides relative to the untreated control.

TABLE 2

| Test Compound | % increase in the ceramides in the epidermis equivalent |
|---|---|
| Vitamin C | 126% |
| Vitamin CP | 148% |

The (cumulative) theoretical value for the mixture of the two vitamin C compounds at 7.5 μg/ml 10 was, therefore: (126+148)/2=137.

However, the real value obtained for the mixture of the two vitamin C compounds, tested at 7.5 μg/ml each, was 170.

This example therefore clearly demonstrates a synergistic action of the vitamin C and vitamin CP immixture on the synthesis of epidermal ceramides, after only 48 hours of treatment.

EXAMPLE 3

Cosmetic Composition:

The following composition according to the invention was conventionally formulated:

| | |
|---|---|
| Octyldodecanol | 0.2% |
| Cyclomethicone | 5% |
| Dimethicone copolyol | 5% |
| Tocopheryl acetate | 1% |
| UV-screening agent | 1% |
| Ascorbic acid | 0.01% |
| Magnesium ascorbyl phosphate | 0.1% |
| Ascorbyl glucoside | 0.1% |
| Glycerin | 3% |
| Disodium EDTA | 0.1% |

-continued

| | |
|---|---|
| pH-adjusting agents | 2.6% |
| Preservatives | 0.4% |
| Gelling agents | 1.2% |
| Water | qs 100% |

A fluid was obtained which may be applied in the morning and/or in the evening to the face to improve the suppleness of the skin and to smooth wrinkles and fine lines.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological composition suited for augmenting the synthesis of epidermal ceramides, and/or improving the barrier function of the skin, and/or treating atopic or seborrhoeic dermatitis, and/or improving the suppleness and/or surface appearance of the skin and/or combating or preventing intrinsic aging of the skin, and/or moisturizing the skin, comprising ascorbic acid in immixture with at least one monosaccharide ester of ascorbic acid and/or at least one metal salt of phosphorylated ascorbic acid, wherein the amount of ascorbic acid is from 0.0001% to 0.01% by weight of said composition; wherein the amount of said at least one monosaccharide ester of ascorbic acid is from 0.001% to 0.1% by weight of said composition and/or the amount of said at least one metal salt of phosphorylated ascorbic acid is from 0.001% to 0.1% by weight of said composition; and wherein said ascorbic acid and monosaccharide ester and/or metal salt are present in a combined, synergistically effective epidermal ceramide synthesis augmenting amount; formulated into a topically applicable, physiologically acceptable vehicle, diluent or carrier therefor.

2. The topically applicable cosmetic/dermatological composition as defined by claim 1, wherein said at least one monosaccharide ester of ascorbic acid is selected from the group consisting of glycosylated, mannosylated, fructosylated, fucosylated, galactosylated, N-acetylglucosaminated and N-acetylmuramic esters of ascorbic acid, and mixtures thereof.

3. The topically applicable cosmetic/dermatological composition as defined by claim 2, wherein said at least one metal salt of phosphorylated ascorbic acid is selected from the group consisting of an ascorbyl phosphate of an alkali metal, an ascorbyl phosphate of an alkaline earth metal and an ascorbyl phosphate of a transition metal.

4. The topically applicable cosmetic/dermatological composition as defined by claim 3, wherein the at least one metal salt of phosphorylated ascorbic acid is magnesium ascorbyl phosphate.

5. The topically applicable cosmetic/dermatological composition as defined by claim 2, wherein said at least one monosaccharide ester of ascorbic acid is 2-O-α-D-glucopyranosyl of L-ascorbic acid or 6-O-β-D-galactopyranosyl of L-ascorbic acid.

6. The topically applicable cosmetic/dermatological composition as defined by claim 1, comprising an aqueous, aqueous/alcoholic or oily solution, or dispersion.

7. The topically applicable cosmetic/dermatological composition as defined by claim 1, comprising an emulsion, a gel, a paste, a solid, spherules, lipid vesicles, a cream, a lotion, a milk, a mousse or foam, a serum, an aerosol, an ointment, or a makeup.

8. The topically applicable cosmetic/dermatological composition as defined by claim 1, further comprising at least one hydrophilic or lipophilic gelling agent, hydrophilic or lipophilic bioaffecting active agent, preservative, antioxidant, solvent, perfume, filler, UV-screening agent, pigment, odor absorber, colorant or combination thereof.

9. A topically applicable cosmetic/dermatological composition suited for augmenting the synthesis of epidermal ceramides, and/or improving the barrier function of the skin, and/or treating atopic or seborrhoeic dermatitis, and/or improving the suppleness and/or surface appearance of the skin and/or combating or preventing intrinsic aging of the skin, and/or moisturizing the skin, comprising ascorbic acid in immixture with at least one monosaccharide ester of ascorbic acid and/or at least one metal salt of phosphorylated ascorbic acid, wherein the amount of ascorbic acid is from 0.0001% to 0.01% by weight of said composition; wherein the amount of said at least one monosaccharide ester of ascorbic acid is from 0.01% to 0.1% by weight of said composition and/or the amount of said at least one metal salt of phosphorylated ascorbic acid is from 0.01% to 0.1% by weight of said composition; and wherein said ascorbic acid and monosaccharide ester and/or metal salt are present in a combined, synergistically effective epidermal ceramide synthesis augmenting amount; formulated into a topically applicable, physiologically acceptable vehicle, diluent or carrier therefor.

10. The topically applicable cosmetic/dermatological composition as defined by claim 9, wherein said at least one monosaccharide ester of ascorbic acid is selected from the group consisting of glycosylated, mannosylated, fructosylated, fucosylated, galactosylated, N-acetylglucosaminated and N-acetylmuramic esters of ascorbic acid, and mixtures thereof.

11. The topically applicable cosmetic/dermatological composition as defined by claim 10, wherein said at least one metal salt of phosphorylated ascorbic acid is selected from the group consisting of an ascorbyl phosphate of an alkali metal, an ascorbyl phosphate of an alkaline earth metal and an ascorbyl phosphate of a transition metal.

12. The topically applicable cosmetic/dermatological composition as defined by claim 11, wherein the at least one metal salt of phosphorylated ascorbic acid is magnesium ascorbyl phosphate.

13. The topically applicable cosmetic/dermatological composition as defined by claim 10, wherein said at least one monosaccharide ester of ascorbic acid is 2-0-α-D-glucopyranosyl of L-ascorbic acid or 6-O-β-D-galactopyranosyl of L-ascorbic acid.

14. The topically-applicable cosmetic/dermatological composition as defined by claim 9, comprising an aqueous, aqueous/alcoholic or oily solution, or dispersion.

15. The topically applicable cosmetic/dermatological composition as defined by claim 9, comprising an emulsion, a gel, a paste, a solid, spherules, lipid vesicles, a cream, a lotion, a milk, a mousse or foam, a serum, an aerosol, an ointment, or a makeup.

16. The topically applicable cosmetic/dermatological composition as defined by claim 9, further comprising at least one hydrophilic or lipophilic gelling agent, hydrophilic or lipophilic bioaffecting active agent, preservative, antioxidant, solvent, perfume, filler, UV-screening agent, pigment, odor absorber, colorant or combination thereof.

17. A topically applicable cosmetic/dermatological composition suited for augmenting the synthesis of epidermal ceramides, and/or improving the barrier function of the skin, and/or treating atopic or seborrhoeic dermatitis, and/or improving the suppleness and/or surface appearance of the skin and/or combating or preventing intrinsic aging of the skin, and/or moisturizing the skin, comprising ascorbic acid in immixture with ascorbyl glucoside and/or magnesium ascorbyl phosphate, wherein the amount of ascorbic acid is from 0.0001% to 0.01% by weight of said composition; wherein the amount of ascorbyl glucoside is from 0.001% to 0.1% by weight of said composition and/or the amount of magnesium ascorbyl phosphate is from 0.001% to 0.1% by weight of said composition; and wherein ascorbic acid, ascorbyl glucoside and/or magnesium ascorbyl phosphate are present in a combined synergistically effective epidermal ceramide synthesis augmenting amount; formulated into a topically applicable, physiologically acceptable vehicle, diluent or carrier therefor.

18. The topically applicable cosmetic/dermatological composition as defined by claim 17, further comprising at least one hydrophilic or lipophilic gelling agent, hydrophilic or lipophilic bioaffecting active agent, preservative, antioxidant, solvent, perfume, filler, UV-screening agent, pigment, odor absorber, colorant or combination thereof.

19. The topically applicable cosmetic/dermatological composition as defined by claim 17, comprising an emulsion, a gel, a paste, a solid, spherules, lipid vesicles, a cream, a lotion, a milk, a mousse or foam, a serum, an aerosol, an ointment, or a makeup.

20. The topically applicable cosmetic/dermatological composition as defined by claim 17, comprising an aqueous, aqueous/alcoholic or oily solution, or dispersion.

21. A topically applicable cosmetic/dermatological composition suited for augmenting the synthesis of epidermal ceramides, and/or improving the barrier function of the skin, and/or treating atopic or seborrhoeic dermatitis, and/or improving the suppleness and/or surface appearance of the skin and/or combating or preventing intrinsic aging of the skin, and/or moisturizing the skin, comprising ascorbic acid in immixture with ascorbyl glucoside and/or magnesium ascorbyl phosphate, wherein the amount of ascorbic acid is from 0.0001% to 0.01% by weight of said composition; wherein the amount of ascorbyl glucoside is from 0.01% to 0.1% by weight of said composition and/or the amount of magnesium ascorbyl phosphate is from 0.01% to 0.1% by weight of said composition; and wherein ascorbic acid, ascorbyl glucoside and/or magnesium ascorbyl phosphate are present in a combined synergistically effective epidermal ceramide synthesis augmenting amount; formulated into a topically applicable, physiologically acceptable vehicle, diluent or carrier therefor.

22. The topically applicable cosmetic/dermatological composition as defined by claim 21, further comprising at least one hydrophilic or lipophilic gelling agent, hydrophilic or lipophilic bioaffecting active agent, preservative, antioxidant, solvent, perfume, filler, UV-screening agent, pigment, odor absorber, colorant or combination thereof.

23. The topically applicable cosmetic/dermatological composition as defined by claim 21, comprising an emulsion, a gel, a paste, a solid, spherules, lipid vesicles, a cream, a lotion, a milk, a mousse or foam, a serum, an aerosol, an ointment, or a makeup.

24. The topically-applicable cosmetic/dermatological composition as defined by claim 21, comprising an aqueous, aqueous/alcoholic or oily solution, or dispersion.

25. A topically applicable cosmetic/dermatological composition suited for augmenting the synthesis of epidermal ceramides, and/or improving the barrier function of the skin, and/or treating atopic or seborrhoeic dermatitis, and/or improving the suppleness and/or surface appearance of the skin and/or combating or preventing intrinsic aging of the skin, and/or moisturizing the skin, comprising ascorbic acid in immixture with ascorbyl glucoside and magnesium ascorbyl phosphate, wherein the amount of ascorbic acid is from 0.0001% to 0.01% by weight of said composition; wherein the amount of ascorbyl glucoside is from 0.001% to 0.1% by weight of said composition and the amount of magnesium ascorbyl phosphate is from 0.001% to 0.1% by weight of said composition; and wherein ascorbic acid, ascorbyl glucoside and magnesium ascorbyl phosphate are present in a combined synergistically effective epidermal ceramide synthesis augmenting amount; formulated into a topically applicable, physiologically acceptable vehicle, diluent or carrier therefor.

26. The topically applicable cosmetic/dermatological composition as defined by claim 25, further comprising at least one hydrophilic or lipophilic gelling agent, hydrophilic or lipophilic bioaffecting active agent, preservative, antioxidant, solvent, perfume, filler, UV-screening agent, pigment, odor absorber, colorant or combination thereof.

27. The topically applicable cosmetic/dermatological composition as defined by claim 25, comprising an emulsion, a gel, a paste, a solid, spherules, lipid vesicles, a cream, a lotion, a milk, a mousse or foam, a serum, an aerosol, an ointment, or a makeup.

28. The topically-applicable cosmetic/dermatological composition as defined by claim 25, comprising an aqueous, aqueous/alcoholic or oily solution, or dispersion.

* * * * *